United States Patent [19]

Augurt et al.

[11] 4,033,938

[45] July 5, 1977

[54] POLYMERS OF UNSYMMETRICALLY SUBSTITUTED 1,4-DIOXANE-2,5-DIONES

[75] Inventors: Thomas Anthony Augurt, Stamford, Conn.; Michael Norman Rosensaft, Monsey; Vincent Anthony Perciaccante, Long Island, both of N.Y.

[73] Assignee: American Cyanamid Company, Stamford, Conn.

[22] Filed: Mar. 14, 1975

[21] Appl. No.: 558,527

Related U.S. Application Data

[62] Division of Ser. No. 435,365, Jan. 21, 1974, abandoned.

[52] U.S. Cl. .................. 260/78.3 R; 260/340.2
[51] Int. Cl.$^2$ ........................... C08G 63/08
[58] Field of Search ............. 260/78.3 R, 340.2

[56] References Cited

UNITED STATES PATENTS

| | | | |
|---|---|---|---|
| 3,268,487 | 8/1966 | Klootwijk | 260/78.3 |
| 3,440,225 | 4/1969 | Sattler et al. | 260/78.3 |
| 3,442,871 | 5/1969 | Schmitt et al. | 260/78.3 |
| 3,636,956 | 1/1972 | Schneider | 128/335.5 |
| 3,839,297 | 10/1974 | Wasserman et al. | 260/78.3 R |

Primary Examiner—Donald E. Czaja
Assistant Examiner—E. A. Nielsen
Attorney, Agent, or Firm—Charles F. Costello, Jr.

[57] ABSTRACT

Unsymmetrically 3,6-substituted 1,4-dioxane-2,5-diones may be polymerized to give living-tissue absorbable, hydrolytically degradable surgically useful polymers. These polymers have predominantly regular rather than random spacings of side chains, may be stereoregular and tend toward higher crystallinity than randomly sequenced polymers. A polymer of 3-methyl-1,4-dioxane-2,5-dione has the same empirical formula as an equimolecular copolymer of lactic and glycolic acid but has unique physical properties resulting from its more regular steric configuration. Polymers and copolymers of 3- and 3,6-unsymmetrically substituted 1,4-dioxane-2,5-diones have surgically useful mechanical properties. On implantation, in living mammalian tissue, the polymers are absorbed, and replaced by living tissue.

5 Claims, No Drawings

POLYMERS OF UNSYMMETRICALLY SUBSTITUTED 1,4-DIOXANE-2,5-DIONES

CROSS REFERENCES

This is a division of application Ser. No. 435,365, filed Jan. 21, 1974, now abandoned. Another division thereof, Ser. No. 558,529, filed March 14, 1975, is now U.S. Pat. No. 3,960,152, June 1, 1976, "SURGICAL SUTURES OF UNSYMMETRICALLY SUBSTITUTED 1,4-DIOXANE-2,5-DIONES".

BACKGROUND OF THE INVENTION

This invention relates to unsymmetrically substituted 1,4-dioxane-2,5-diones, methods of making them, and more particularly to polymers, which polymers are either homopolymers of the unsymmetrically substituted 1,4-dioxane-2,5-diones or copolymers, and which polymers are compatible with living mammalian tissue, particularly human tissue, and which materials can be used surgically and are biologically degradable into tissue compatible components which are absorbed by living tissues. It is presently postulated that the primary degradation of the polymer is by hydrolytic fission into products which can be carried away by the living tissue and which products are degradable to excretable components or are themselves excretable. Because of the surgical demand for sutures, absorbable fabrics, gauzes, bone pins, etc. whose absorption and strength characteristics vary, it is desirable that a spectrum of strength and absorbability be provided to meet surgical demands for various procedures.

DESCRIPTION OF THE PRIOR ART

U.S. Pat. No. 2,518,456, Fein and Fisher, Aug. 15, 1950, PREPARATION OF ACYLOXY CARBOXYLIC ACIDS FROM ESTERS OF HYDROXY CARBOXYLIC ACIDS, discloses preparing

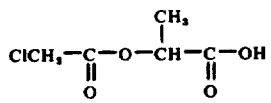

there called chloroacetoxypropionic acid (which may be also properly named as O-(chloroacetyl)-lactic acid or a α-(chloroacetoxy)-propionic acid) by transesterification using an acid catalyst such as concentrated sulfuric acid with chloroacetic acid and ethyl lactate.

U.S. Pat. No. 2,676,945, Higgins, Apr. 27, 1954, CONDENSATION POLYMERS OF HYDROXYACETIC ACID, discloses strong orientable fibers of polyhydroxyacetic acid condensate (polyglycolic acid) having an intrinsic viscosity of 0.5 to 1.2.

U.S. Pat. No. 2,758,987, Salzberg, Aug. 14, 1956, OPTICALLY ACTIVE HOMOPOLYMERS CONTAINING BUT ONE ANTIPODAL SPECIES OF AN ALPHA-MONOHYDROXY MONOCARBOXYLIC ACID, discloses forming high molecular weight optically active, cold-drawable, polymers from one antipodal species of alpha-hydroxypropionic acid (lactic acid).

U.S. Pat. No. 3,268,487, Klootwijk, Aug. 23, 1966, PROCESS FOR POLYMERIZATION OF LACTIDES, discloses catalyst systems and the polymerization of symmetrical lactides to give polymers with the recurring unit

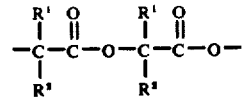

where $R^1$ and $R^2$ are hydrogen atoms or alkyl, cycloalkyl, haloalkyl, hydroxyalkyl, alkoxy, phenol, alkaryl, hydroxphenyl, or haloaryl radicals. Copolymers, including block copolymers are shown. (Col. 1, lines 57–66).

U.S. Pat. No. 3,297,033, Schmitt and Polistina, Jan. 10, 1967, SURGICAL SUTURES, discloses polyhydroxyacetic ester absorbable sutures. The material is also called polyglycolic acid, and is disclosed as permitting small quantities of comonomers to be present, such as dl-lactic acid, its optically active forms, homologs and analogs. A small quantity is recognized by the art as up to 15%, as shown by U.S. Pat. No. 2,668,162, Feb. 2, 1954, PREPARATION OF HIGH MOLECULAR WEIGHT POLYHYDROXY-ACETIC ESTER.

Many uses of polyglycolic acid for surgical purposes are disclosed in said U.S. Pat. No. 3,297,033 and continuations-in-part thereof including: U.S. Pat. Nos. 3,463,158, Infra; 3,620,218, Infra; 3,739,773, June 19, 1973 - POLYGLYCOLIC PROSTHETIC DEVICES and U.S. Ser. No. 365,656, May 31, 1973, SURGICAL DRESSINGS OF ABSORBABLE POLYMERS.

U.S. Pat. No. 3,303,177, Natta, Peraldo and Farina, Feb. 7, 1967, SUBSTANTIALLY LINEAR, REGULARLY HEAD-TO-TAIL POLYMERS OF DEUTERATED AND TRITIATED MONOMERS AND PROCESS FOR PRODUCING THE SAME, discloses the important effect of high regularity of steric structure as well as high regularity of chemical structure on the characteristics of polymers. A nomenclature for such polymers is set forth.

U.S. Pat. No. 3,463,158, Schmitt and Polistina, Aug. 26, 1969, POLYGLYCOLIC ACID PROSTHETIC DEVICES, discloses surgical uses of polyglycolic acid, and incorporates definitions of some terms.

U.S. Pat. No. 3,492,325, Thompson, Jan. 27, 1970, PRODUCTION OF α-HYDROXY ACIDS AND ESTERS, discloses the conversion of α-keto acetals into α-hydroxy acids and esters, -hydroxy acids and esters, including lactides. The lactides produced are symmetrical.

U.S. Pat. No. 3,620,218, Schmitt and Polistina, Nov. 16, 1971, CYLINDRICAL PROSTHETIC DEVICES OF POLYGLYCOLIC ACID, lists many surgical uses of polyglycolic acid.

U.S. Pat. No. 3,626,948, Glick and McPherson, Dec. 14, 1971, "Absorbable Polyglycolic Acid Suture of Enhanced In-Vivo Strength Retention" discloses heating under vacuum, under specified conditions to remove volatile components to give longer in-vivo strength retention to polyglycolic acid surgical protheses, including sutures.

U.S. Pat. No. 3,636,956, Schneider, Jan. 25, 1972, "Polylactide Sutures", discloses polylactides which may contain up to 70 mole percent glycolide (Col. 12, line 4), and mentions other comonomers, including tetramethyl glycolide. (Column 2, line 24). Lactide may be considered to be a symmetrical dimethylglycolide. Schneider prefers polylactides of one antipodal species, usually poly L(-) lactide.

U.S. Pat. No. 3,736,646, Schmitt, et al., June 5, 1973, METHOD OF ATTACHING SURGICAL NEE- DLES TO MULTIFILAMENT POLYGLYCOLIC ACID ABSORBABLE SUTURES, discloses surgical elements of a copolymer containing from 15 to 85 mol percent glycolic acid and 85 to 15 mol percent lactic acid.

U.S. Pat. No. 3,763,190, Ross, Barrett, and McDonald, October 2, 1973, PREPARATION OF PURE GLYCOLIDE, discloses the ring closure of O-chloroacetylglycolic acid as the sodium salt to give glycolide.

Sporzynski, Kocay and Briscoe, A NEW METHOD OF PREPARING GYLCOLLIDE, Recueil, 68, 613–618, (1949)relates the "thermal decomposition of sodium chloracetate under reduced pressure in the presence of copper gave glycollide . . ."

Chujo, Kobayashi, Suzuki, Tokuhara and Tanabe RING-OPENING POLYMERIZATION OF CYLCOLIDE, Die Makromolekulare Chemi, 100, 262–266, (1967) shows the preparation of glycolide by the elimination of sodium chloride from sodium monochloroacetate

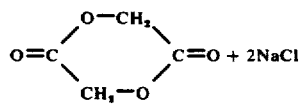

The disclosures of the above patents and articles, particularly on methods of manufacture and purification of components and of surgical uses for hydrolytically degradable tissue absorbable polymers, are hereby herein incorporated by this reference thereto.

NOMENCLATURE

Hydroxyacetic acid bears the trivial name of glycolic acid.

2-Hydroxypropanoic acid, or α-hydroxypropanoic acid bears the trivial name of lactic acid. Lactic acid has the formula $CH_3CHOHCOOH$, and has an asymmetric carbon atom, and, hence, may exist in two different optically active forms, commonly called D(−)lactic acid and L(+)lactic acid. Where not otherwise specified or incorporated from context, the term lactic acid refers to the equimolecular or racemic mixture.

A lactide is defined as the product from the internal cyclic esterification of two molecules of an α-hydroxy alkanoic acid. If the α-hydroxy alkanoic acid is lactic acid, the product is lactide itself, which gives its name to the series. Generically, the reaction is

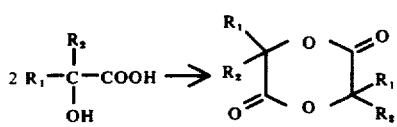

where $R_1$ and $R_2$ are each separately hydrogen or alkyl.

From the nature of the reaction, such lactide is essentially symmetrical, that is, it has two identical $R_1$ groups and two identical $R_2$ groups on the six-membered ring. The compounds in which $R_1$ is hydrogen are much the more common.

These compounds may be named by systematic nomenclature, for instance, the lactide of lactic acid, with $R_1$ being methyl and $R_2$ being hydrogen is properly named and indexed as 3,6-dimethyl-1,4-dioxane-2,5-dione.

In the present invention, the substitution is not symmetrical and, hence, the products are not properly classed as lactides, but are named as 3-, or 3,6-substituted 1,4-dioxane-2,5-diones.

The simplest, and what can be considered as the parent to the class is 3-methyl-1,4-dioxane-2,5-dione, which can be given the trivial name of monomethyglycolide. Another name is 3-methyl-2,5-diketo-1,4-dioxane. This compound has part of the attributes of glycolide and some of lactide, but, uniquely, is adapted to give controlled and ordered polymers which empirically resemble a copolymer of glycolide and lactide, but have an ordered structure imparting unique and desirable properties.

When glycolide is homopolymerized, the product is called homopolymeric poly(hydroxyacetic acid) or poly(glycolic acid) or polyglycolide. The individual units in the polymer chain are oxyacetyl radicals

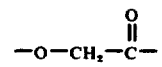

which may be called glycolic acid residue, or glycolic acid units, or glycolic acid radicals or glycolic acid linkages, even though in polymerization water eliminated in forming the resultant polyester. For convenience, the term glycolic acid unit is usually used herein.

Similarly, when lactide is homopolymerized, the product is called homopolymeric poly(lactic acid) or poly(alpha-hydroxypropionic acid) or polylactide. The individual units in the polymer chain are 2-oxypropionyl radicals

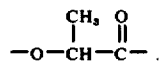

These can be called lactic acid residues or lactic acid units, or lactic acid radicals, or lactic acid linkages.

For convenience, the term lactic acid is usually used herein. The steric configuration is specified if significant and not apparent from context. The steric configuration of the product is normally that of the starting materials. If the additional regularity resulting from a single antipode is desired, an appropriate starting material is selected.

When polymerized into chains, three consecutive glycolic acid units are abbreviated —G-G-G- and three consecutive lactic acid units are abbreviated —-L-L-L-. A regularly alternating polymer of glycolic acid units and lactic acid units is abbreviated —-G-L-G-L-G-L—. Other orders are similarly represented by the sequence of capital letters.

In places, hexafluoroacetone sequihydrate is abbreviated as HFAS; hexafluoroisopropanol is abbreviated as HIPA; polyglycolic acid) is abbreviated as PGA and 3-methyl-1,4-dioxane-2,5-dione can be abbreviated as MDD.

To be consistent, the name O-chloroacetyl-L-lactic acid is used, with D,L- or L or D being so designated where appropriate for the formula

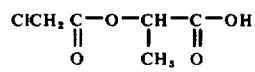

Other common names include L-2-(chloroacetoxy)-propionic acid and L-α-(chloroacetoxy)-propionic acid.

In copolymerization of two monomers, depending upon the catalyst used and reaction conditions, the relative rates of reactivity vary, and one of the monomers usually tends to polymerize more rapidly than the other.

For example, if an equimolecular mixture of glycolide and lactide is polymerized, the glycolide tends to link to the growing chains more readily giving relatively long sequences of glycolic acid units with occasional short sequences of lactic acid units and as the concentration of the unreacted components change, the ratio of lactide to glycolide increases and the polymer being formed may contain more nearly equal numbers of glycolic acid units and lactic acid units. If the polymerization is stopped before completion, a disproportionately large amount of unreacted lactide is present in the reaction vessel. The occurence of pairs of glycolic acid units and pairs of lactic acid units is basically random in nature with a bias towards the preponderance of glycolic acid units in the first portions of chains formed and an increasing proportion of lactic acid unit in those portions of the chains last found.

If carried to completion, the last portions of chains formed are predominantly of pairs of lactic acid units as a minimum of glycolide remains to link to the chains.

Under the usual conditions of polymerization, a random order significantly predominates and, hence, the product tends to have more of an amorphous rather than crystalline character. For crystallinity to occur, extensive lengths of the chain need steric regularity. For instance, a regular brick wall can be easily built in any one of the number of patterns from ordinary bricks which frequently have a size of 2 inches x 4 inches x 8 inches including the mortar. On the other hand, random stones or a multitude of sizes do not so readily lend themselves to an ordered structure. Analogously with polymer molecules, if the side groups occur in a strictly random sequence, the crystallinity of a product is decreased as compared with polymers formed with strictly regular side group spacing.

The present invention relates to the use of unsymmetrically substituted 1,4-dioxane,-2,5-diones which in polymerization gives two different units of alpha-hydroxy alkanoic acid precursors, but which are very well ordered.

SUMMARY OF THE INVENTION

This invention relates to unsymmetrically substituted 1,4-dioxane-2,5-diones, precursors of such dioxanediones, and polymers formed from such dioxanediones. In the simplest such unsymmetrically substituted dioxanedione, 3-methyl-1,4-dioxane-2,5-dione, a lactic acid unit, and a glycolic acid unit, are in effect cyclized together, and in polymerization when such a ring is opened and added to a polymer chain, a lactic acid unit and a glycolic acid unit are adjacent in the polymer chain. If the ring opening and addition is strictly uniform, the final product will have regularly alternating lactic acid units and glycolic acid units. If polymerization is random, because there is a glycolic acid unit attached to each lactic acid unit, not more than two glycolic acid units or two lactic acid units will be adjacent in the chain formed.

Because hydrolytic fission of the polymer chain is more probable adjacent a glycolic acid unit, and even more probable between two such glycolic acid units, a minimum of long blocks of lactic units gives more rapid hydrolytic fission, and polymers having adjacent glycolic acid units are absorbed by tissue even more rapidly than polymers having strictly alternating glycolic acid units and lactic acid units.

Copolymerization of some glycolide with the 3-methyl-1,4-dioxane-2,5-dione increases susceptibility to hydrolytic fission.

If polymerization of a mixture of glycolic acid and lactic acid is used to form a copolymer with removal of water, the sequence of units in the final copolymer chain will be somewhat random, with the first portions formed tending to include more glycolic acid units. Because in polymerization such chains are not always identical and because of the difficultly of analysis, it is not always readily possible to ascertain the exact order in a chain, but the general properties of the polymer are the items of interest and it is found that the additional regularity imparted to the chain by the use of the unsymmetrically substituted 1,4-dioxane-2,5-diones results in polymers which are both chemically and terically more uniform.

The unsymmetrically substituted 1,4-dioxane-2,5-diones of this invention are of importance in the medical field because their polymers, including homopolymers and copolymers with various lactides including glycolide and lactide, are useful as surgical elements as later described, but, additionally, the unsymmetrically substituted 1,4-dioxane-2,5-diones are excellent weak acidifying agents. They may be used in such materials as baking powders or for the control of pH in boiler waters. They may also be used in non-aqueous systems for the neutralization of alkali. Because the side chains may vary from methyl to long chain alkyl, including branched chains, unsaturated chains, aryl or aralkyl, and which may include halogen, alkoxy, aryloxy, aralkoxy, ether, ester and amide groups, as substituents on the side chains, the relative distribution between aqueous and solvent components in a system can be varied as well as water solubility or oil and solvent solubility so that the 1,4-dioxane-2,5-dione is distributed in a desired location and also because the size and location of the side chains affects the rate of hydrolysis, the acidity of the system, the rate of availability of acid can be varied over wide limits to meet the requirements of a system and the desires of the operator. The less highly substituted materials are often preferred for medical uses. The broader range of substituents permits more flexibility in pH control, and in biodegradable polymers for use in packaging, etc. The use of side chains with unsaturated linkages permits cross-linked polymers to be formed. This uniformity results in greater strength, more crystallinity, and more readily reproducible and controllable characteristics, which are of interest to a surgeon during use.

By copolymerizing the present 1,4-dioxane-2,5-diones, with either glycolide or lactide, the physical properties of the polymer are altered to more closely resemble that of either polyglycolic acid or polylactic acid respectively and the absorption characteristics may be varied. The length of polymer chain, as shown by the inherent viscosity of the polymer, also is important in determining the rate of hydrolytic degradation in tissues and hence by adjusting both the inherent viscosity and the ratio of components, there is provided a wide range of tissue absorbable surgical components which may be tailored to fit the desires of a surgeon for a particular procedure.

For many purposes, it is desired that the synthetic tissue absorbable polymer maintain its strength for from 2—60 days and then degrade and be absorbed thereafter. Because the disappearance of strength is a gradual function, the loss of strength is apt to start very early in the useful life, but an adequate and useful proportion of strength is maintained for a surgically desirable period of time and the ultimate absorption of the polymer occurs thereafter. Although the polymers having glycolic and lactic acid units are often preferred, dioxanediones are useful in which the substituents are ethyl, propyl, isopropyl, butyl isobutyl, cyclohexyl and phenyl radicals.

One convenient method of making the unsymmetrically substituted 1,4-dioxane-2,5-diones is by the reaction of a substituted acetic acid with an o-hydroxy carboxylic acid to form an acyloxy acid which is ring closed to form the 3,6-substituted-1,4-dioxane-2,5-dione or the 3-substituted-1,4-dioxane-2,5-dione. The equations appear as follows:

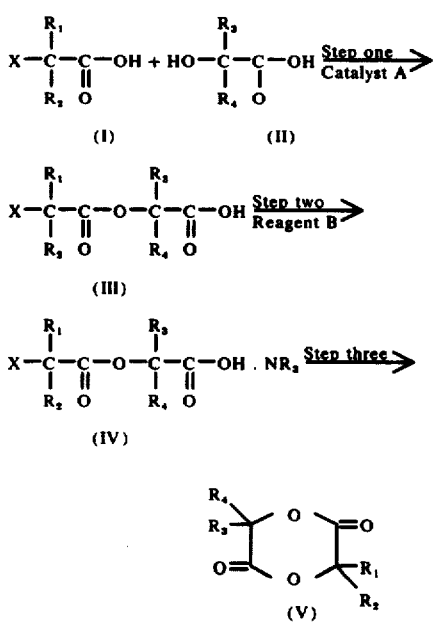

in which $R_1$, $R_2$, $R_3$ and $R_4$ are each hydrogen, alkyl, aryl or arylalkyl and which are chosen so that $R_1$ and $R_2$ are not the same as $R_3$ and $R_4$ and at least one of $R_1$ and $R_3$ has at least one carbon atom. X is a halogen or

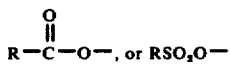

where R is H, alkyl or aryl or aralkyl and the catalyst A for the first step is a strongly acidic catalyst such as concentrated sulfuric acid, p-toluene sulfonic acid, a strongly acidic ion-exchange resin or other material which effectively acts as a strong acid. The reagent B for the second step is conveniently a trialkylamine, such as triethylamine, but may be sodium methylate in methyl alcohol, pyridine or a strongly basic ion-exchange resin. For clarity, a trialkylamine is shown as reagent B in the equation above. In the ring-closing step, step three, heat is usually sufficient in the presence or absence of a solvent or diluent.

In view of the well known propensity for α-hydroxyalkanoic acids in general to cyclize or polymerize and then depolymerize or open the ring, it would be expected that unsymmetrical 1,4-dioxane-2,5-diones would polymerize, depolymerize and split to form symmetrical components which could permit the formation of long blocks of similar units in the final polymer. Fortunately, it is found that such randomization does not occur and that regularity of the acid units in the polymer occurs so that the characteristics can be adapted and tailored to specific uses and reproducibly obtained.

Because of optical activity that can occur if $R_1$ and $R_2$ are different or if $R_3$ and $R_4$ are different, various stereo isomeric components may be obtained and used. It is particularly convenient to use L- or D- or D,L-lactic acid as a starting material. The optically active forms give different melting points and changes in physical characteristics. It is often convenient to use L-lactic acid as a starting material in which case the polymer contains units with the L-configuration. For instance, chloroacetic acid and L-lactic acid may be used as starting materials to give the L from of 3-methyl-1,4-dioxane-2,5-dione.

Other methods of preparing unsymmetrical 1,4-dioxane-2,5-diones include: (a) Cocondensation of two different alpha-hydroxy acids A and B, with removal of water to form a low-molecular weight random copolymer, and then heating this copolymer with a transesterification catalyst to form a mixture of cyclic dimers. The desired unsymmetrical cyclic dimer is isolated by functional distillation. (b) Glycolide is chlorinated to give 3-chloro-1,4-dioxane-2,5-dione and and this is treated with a metal alkyl or metal aryl to give 3-alkyl or 3-aryl-1,4-dioxane-2,5-dione.

In general, the surgical uses of the polymers produced in accordance with the present invention are similar to those previously taught for polyglycolic acid. These uses are extremely varied.

For clarity and explanation, certain terms are defined and representative uses given for the novel polymers.

A "filament" is a single, long, thin flexible structure of a non-absorbable or absorbable material. It may be continuous or staple.

"Staple" is used to designate a group of shorter filaments which are usually twisted together to form a longer continuous thread.

An absorbable filament is one which is absorbed, that is, digested or dissolved, in living mammalian tissue.

A "thread" is a plurality of filaments, either continuous or staple, twisted together.

A "strand" is a plurality of filaments or threads twisted, plaited, braided, or laid parallel to form a unit for further construction into a fabric, or used per se, or a monofilament of such size as to be woven or used independently.

A "fabric" is a three dimensional assembly of filaments, which may be woven, knitted, felted or otherwise formed into a flexible sheet having two layer dimensions and a thinner thickness dimension. A fabric may be cut to a desired size before or at the time of use.

Except where limited specifically or by context, the word fabric includes both absorbable and non-absorbable cloth, or a fabric or cloth that is partially of absorbable polymer.

A "dressing" is a woven, knitted, felted or braided fabric, of at least one layer, which is designed to protect a wound and favor its healing. As used herein, the term dressing includes bandages, insofar as they contact the wound itself. The dressing may be entirely internal.

A "bandage" is a strip of gauze, or other material used to hold a dressing in place, to apply pressure, to immobilize a part, to obliterate tissue cavities or to check hemorrhage. Except insofar as the bandage comes in contact with a wound, or the exudate from a wound, there is no need for the bandage to be of absorbable polymer. If the bandage may be in a position where absorbability by living tissue of at least part of the bandage is desirable, at least that part should be of absorbable polymer.

A "respository" is a composite of a medicament and a carrier whereby the medicament is placed in a desired location, and released slowly by the carrier so that the effective therapeutic action of the medicament is extended. Slowly digestible drug release devices, including pills and pellets, may be inserted subcutaneously, or orally, or into any body cavity where slowed release of the medicament is desired. Digestible carriers are preferred. The digestion may be in the intestinal tract or in tissue depending on the desired administrative site. An absorbable polymer is chosen whose digestive rate releases the medicament at a desired rate.

The dressing may be in part directive of growth, as, for example, in nerve tissue, which grows slowly, and as a result has regeneration impaired by the more rapid growth of scar tissue which can block the growth of the nerve tissue. With a wrap-around sheath of absorbable polymer fabric or a split tube used to support, place, hold and protect; regeneration of nerve tissue and function is greatly aided. Other factors may inhibit regeneration of nerve tissue or function, but with the exclusion of scar tissue, such other factors may be separately treated.

For different purposes and in different types of tissue the rate of absorption may vary. In general, an absorbable suture or solid load bearing prosthesis should have as high a portion of its original strength as possible for at least three days, and sometimes as much as thirty days or more, and preferably should be completely absorbed by muscular tissue within from forty-five to ninety days or more depending on the mass of the cross-section. The rate of absorption in other tissues may vary even more.

For dressings, strength is often a minimal requirement. Some dressings, as for instance, on a skin abrasion, may need strength for only a few hours, until a scab forms, and rapid decrease of strength and absorption is an advantage so that when the scab is ready to fall off, the dressing does not cause a delay. For burns, and larger lesions, strength and reinforcement may be desired for a longer period.

In common with many biological systems, the requirements are not absolute and the rate of absorption as well as the short-term strength requirement varies from patient to patient and at different locations within the body, as well as with the thickness of the section of the polymer.

The absorbable polymer may be formed as tubes or sheets for surgical repair and may also be spun as thin filaments and woven or felted to form absorbable sponges or absorbable gauze, or used in conjunction with other compressive structures as prosthetic devices within the body of a human or animal where it is desirable that the structure have short-term strength, but be absorbable. The useful embodiments include tubes, including branched tubes or Tees, for artery, vein or intestinal repair, nerve splicing, tendon splicing, sheets for tying up and supporting damaged kidney, liver and other intestinal organs, protecting damaged surface areas such as abrasions, particularly major abrasions, or areas where the skin and underlying tissues are damaged or surgically removed.

In surgical techniques involving internal organs, hemorrhage may be a major problem. Some of the organs have such tissue characteristics that it is very difficult to use sutures or ligatures to prevent bleeding. For example, the human liver may suffer traumatic damage or exhibit tumors or for other reasons require surgery. In the past it has been very difficult to excise part of the liver or to suture the liver without the combined problems of the sutures cutting out and hemorrhage at the surface causing such major complications as to either prevent surgery or cause an unfavorable prognosis.

It is now found that a sponge or pad or velour of the present absorbable polymer may be used to protect the surface and permit new feats of surgical intervention. For instance, filaments may be formed into a woven gauze or felted sponge or a velour, preferably the construction is fairly tight by textile standards, and such sponge may be placed on the surface of the bleeding organ such as the liver or a lung with either gentle suturing or with ties in the nature of ligatures to hold the element in position with a certain amount of body fluids flowing into the sponge and being absorbed, which results in hemostasis and prevention of further loss of body fluids. If a liver or lung is so repaired, the organ may be replaced in the body cavity and the wound closed.

Where surgically useful, the sponge or fabric can be used as a bolster to prevent a suture from cutting out. For instance, if the liver is to be sutured, an absorbable polymer pad can be placed on the surfaces to reinforce the tissue and prevent the suture from cutting into rather than retaining the tissue. Such pads of gauze or felt protect tissue from cutting.

Absorbable pads, bandages or sponges are extremely useful in surgical techniques in which it is the intent to remove the major portion or all of such sponges, felt or pads but, through inadvertence or accident, part of it may remain. For instance, in a surgical operation one of the problems which arises is the lint from cotton sponges remaining in the wound. If absorbable polymer sponges are used, any small fragments which are accidentally displaced are absorbed without incident and even if a sponge is left in the wound, the deleterious effects are minimal.

The use of a synthetic absorbable polymer as a sponge or pad is particularly advantageous for surface abrasions. In the past it has been necessary to put on a dressing and avoid having the non-absorbable dressing grow into the tissue at all costs. If elements of an absorbable polymer gauze are beneath the regenerating tissue level, the tissue will regenerate and absorb the polymer with the residual polymer in the scab falling off when the scab is displaced.

The dressing that contacts tissue should be sterile. A strippable sterile package is a convenient storage system to maintain sterility between the time of manufacture and time of use.

Even in cosmetic surgery or skin surgery, where in the past it has been quite customary to use silk sutures and, after the tissue is regenerated sufficient to be self retaining, remove the sutures so that they do not leave scars, the use of synthetic absorbable polymer sutures now permits implantation of sutures through the skin with the part below the skin surface being absorbed and the part above the skin surface falling off. The resulting minimal degree of scarring at the skin surface is highly advantageous.

In surgery various tissues need to be retained in position during healing. Defects and wounds of the abdominal wall, chest wall and other such tissues need to be reconstructed. For a hernia, a permanent splice or reinforcement is often desired as shown in Usher, U.S. Pat. Nos. 3,054,406, SURGICAL MESH, or 3,124,136, METHOD OF REPAIRING BODY TISSUE. For some surgical procedures, a temporary reinforcing is desired to provide strength while body tissues are healing; and after the body tissues have assumed the load, foreign components are no longer desired. Tissue retention using the general techniques disclosed in the Usher patents, supra, are readily accomplished using either an absorbable synthetic polymer monofilament or polyfilament fabric or mesh or by using a nonabsorbable material such as polyethylene or polypropylene or polyester woven as a bicomponent mesh or kit with an absorbable synthetic polymer. The use of a bicomponent fabric has the advantage of giving additional early strength for holding the tissues in position during initial regeneration with the absorbable portions being absorbed, thus permitting body tissues to invade and reinforce the permanent mesh.

In common with other surgical procedures, it is often desirable that a bicomponent structure be used which provides the spacing desired for non-absorbable elements, with the absorbable synthetic polymer element holding the structure in a desired geometrical configuration at the start of the healing process. As the element is absorbed, regenerating tissue invades and replaces the dissolved synthetic polymer so that the non-absorbed element is left in a desired configuration, interlaced with living tissue in a stress-transferring relationship. The choice of a non-absorbable reinforcement, a partially absorbable reinforcement, or a completely absorbable reinforcement is a matter of surgical judgment, based upon the condition of the patient, the body structure under treatment, and other medical factors.

For instance, a synthetic absorbable polymer sponge may be used in a cavity after tooth extraction to stanch the flow of blood. The sponge is either absorbed by regenerating tissue, or disintegrates into the mouth, permitting improved recovery after extractions.

The medical uses of the polymers of the present invention include, but are not necessarily limited to:

A. Absorbable polymer alone

1. Solid Products, molded or machined
   a. Orthopedic pins, clamps, screws and plates
   b. Clips (e.g., for use as hemostat)
   c. Staples
   d. Hooks, buttons and snaps
   e. Bone substitute (e.g., mandible prosthesis)
   f. Needles
   g. Non-permanent intrauterine devices (spermicide)
   h. Temporary draining or testing tubes or capillaries
   i. Surgical instruments
   j. Vascular implants or supports
   k. Vertebral discs
   l. Extracorporeal tubing for kidney and heart-lung machines
2. Fibrillar Products, knitted or woven, including velours
   a. Burn dressings
   b. Hernia patches
   c. Absorbent paper os swabs
   d. Medicated dressings
   e. Facial substitutes
   f. Gauze, fabric, sheet, felt or sponge for liver hemostasis
   g. Gauze bandages
   h. Dental packs
   i. Surgical sutures
3. Miscellaneous
   a. Flake or powder for burns or abrasions
   b. Foam as absorbable prosthesis
   c. Substitute for wire in fixations
   d. Film spray for prosthetic devices B. Absorbable polymer in Combination with other Products 1. Solid Products, molded or machined
   a. Slowly digestible ion-exchange resin
   b. Slowly digestible drug release device (pill, pellet) as a repository, oral or implanted or intravaginal
   c. Reinforced bone pins, needles, etc.
2. Fibrillar Products
   a. Arterial graft or substituents
   b. Bandages for skin surfaces
   c. Burn dressings (in combination with other polymeric films)
   d. Coated sutures (i.e., a coating on a suture of this polymer)
   e. A coating of the present polymer on a suture of other material
   f. A two component suture, one being the present polymer, the components being spun or braided together
   g. Multicomponent fabrics or gauzes, the other component of which may be non-absorbable, or more rapidly absorbable.

The synthetic character and hence predictable formability and consistency in characteristics obtainable from a controlled process are highly desirable.

One convenient method of sterilizing synthetic absorbable polymer prosthesis is by heat under such conditions that any microorganisms or deleterious materials are rendered inactive. Another common method is to sterilize using a gaseous sterilizing agent such as ethylene oxide. Other methods of sterilizing include radiation by X-rays, gamma rays, neutrons, electrons, etc., or high intensity ultrasonic vibrational energy or combinations of these methods. The present synthetic absorbable polymers may be sterilized by any of these methods, although there may be an appreciable but acceptable change in physical characteristics.

Controlled release rates are very desirable. Some drugs are injected with the intention that the faster the drug is absorbed, the better. Others need to be emplaced under such conditions that the maximum concentration released is within desired limits, and yet the drug is made available over an extended period of time so that a single implantation can last for whatever length of time is desired for a particular medical procedure. For instance, as a birth control pill, the blood levels of certain steroids are to be maintained at a low level for prolonged periods. The steroid may be dissolved in chloroform, the present polymers added, the mixture dried and tabletted. The polymer, its molecular weight and hydrolytic history affect the relative rate of drug release and absorption of the carrier.

For contraceptive purposes, an effective storage bank may be desired with a prolonged release time. The medicament containing absorbable polymer may be shaped and used as an intrauterine contraceptive device, having the advantages of both shape and the released medicament, and additionally an inherently limited effective life. With other steriods used for the treatment of pathological conditions, the choice may be that the entire dosage is released uniformly over a period of from 1 to 30 days, or so. For other drugs the release period desired may be even more widely variable. For some antibiotics an effective concentration for 1 to 2 days is preferred for control of some pathogens.

Additional materials such as silicones may be coated upon the polymer repository where it is desired that the release rate be further delayed. For instance, there are pathological conditions under which the release of a drug or hormone may be desired for the remaining life of a subject.

Sterility is essential in the subcutaneous implants, and desirable in oral forms. If the medicament is adaptable to radiation, heat, or ethylene oxide sterilizing cycles, such may be used. For more labile mdicaments, the absorbable repository forms are made using sterile techniques from sterile components, or a sterilization procedure is chosen which is compatible with the medicament characteristics.

Other substances may be present, such as dyes, antibiotics, antiseptics, anaesthetics, and antioxidants. Surfaces can be coated with a silicone, beeswax, and the like to modify handling or absorption rate.

The absorbable polymer can be spun into fibers and used to form strands. Fibers of about 0.002 inch diameter are particularly convenient for fabrication. Sheets, or tubes from these absorbable polymer are wrapped around nerves, traumatically severed, to protect such nerves from invasive scar tissue growth, while the nerve is regenerating.

The ends or edges of mono-component or bi-component fabrics containing absorbable polymer may be rendered rigid by molding such edges, with or without additional solid absorbable polymer to a desired configuration. It is often easier to insert and retain a flexible fabric prosthetic tube if the end of the tube is of a size and shape to be inserted into the severed end of a vessel.

Becoming of increasing interest and importance is the implantation of cosmetic devices. For example, some women, due to partial surgical removal of breast tissue because of malignancies or traumatic injuries, are left with smaller breasts than are considered desirable. Additionally, some women are not as well naturally endowed as may be required by the styling trends or fashion at a particular time. In the past, among the first surgical contributions to inflation were injections of silicones. The silicones enlarge the appearance of the breast, but inherently remain shiftable and hence the silicone is apt to migrate from the desired location to some other less strategic area.

A non-migrating prosthetic implantation has been used which consists of a plastic sponge or a plastic bag partially filled with a liquid having a viscosity adjusted to simulate that of natural tissue. The bag is implanted through a slit under the breast, to raise the mammary tissue away from the underlying chest wall which permits surgical reconstruction which has a very natural appearance and resilience. See U.S. Pat. No. 3,559,214 for surgical details.

A difficulty that is encountered is the possibility of displacement of such an implanted bag from the location of choice from the effects of gravity or pressure.

If the bag to be used is constructed from a physiologically inert material such as polypropylene or a silicone film, the bag can be formed with a surface roughness in which, through loops, or fusion of filaments of polypropylene or other material there is formed a bag to which the non-absorbable filament are attached. If tissue absorbable polymer fibers as a bi-component material are stiched, woven, felted or otherwise formed into such appendant structures, the elements may be readily emplaced and the tissue absorbable polymer portions are dissolved out with naturally occurring tissue replacing the absorbable polymer and thus becoming intermeshed with the elements attached to the prosthetic bag which interlocks the bag in location in the body tissues, primarily the chest wall, and hence the implanted prosthetic device is firmly locked into the tissues and protected from accidental displacement, maintaining a desired configuration with comfort to the patient.

In one embodiment, the implanted prosthetic device is an implantable bag containing viscous liquid therein, which may be a single cell or a sub-divided cell, with a puncturable area in a selected location so that after implantation, a hypodermic needle may be used to puncture through the skin and intervening, the puncturable area and into the main volume of the prosthetic device which permits hypodermic removal or addition of inflating liquid so that with a minimum inconvenience, time and expense, the enhancing volume may be modified with changing fashions or the desires of the user.

A similarly constructed element using the same conjoint bi-component displacing technique is useful to fill out other areas in which external tissue contours are to be changed. For example, an individual may have been involved in an automobile accident or the victim of a tumor and with the removal of certain tissues, a disfiguring surface configuration remains. By filling in with a prosthetic element of suitable size and shape, the surface configuration can be reconstructed to the great psychological benefit of the subject.

Similar, but solid, devices may be implanted in the nose, chin or ears to modify, restore or correct the surface configuration of the subject. In some instances, it is found that the psychological benefit to the subject far overshadows any surgical risks, costs or inconveniences resulting from the operative technique.

A bi-component system can be used to aid in retaining implanted devices such as internal pacemakers or hearing aids. See U.S. Pat. No. 3,557,775, supra, for details of the surgical aspects.

In the case of extensive superficial abrasions, dressings, frequently gauze, pads or wrappings absorb blood or lymph and present a problem because the gauze dressings stick to the wound or are infiltrated by regenerated tissue. In the past, it has been customary to change dressings frequently to prevent such infiltration. Removing an adherent dressing can be quite painful.

Extensive surface abrasions such as from sliding on a concrete surface after falling off a motorcycle can be debrided and wrapped with a gauze synthetic absorbable polymer. The wound shows a tendency to bleed into the absorbable polymer gauze but the porosity of the gauze aids in rapidly stopping the flow of blood. By using several layers and permitting the blood to at least partially harden, a minimum amount of the absorbable polymer gauze is required and the main protective dressing is of ordinary cotton gauze wrapped around the injured area. A minimum of changing the dressing is required. The outer cotton gauze may be removed for inspection to be sure that infection does not occur, but the absorbable polymer gauze is allowed to remain in position, and partly heals into the tissue, and partly remains above the tissue. Fewer manipulative steps aid in preventing the entrance of new pathogens. After healing, the gauze below the new skin surface absorbs in the body and the non-absorbed gauze and the scab separate readily.

Details of representative syntheses are set forth in the following examples, in which parts are by weight unless otherwise clearly indicated.

EXAMPLE 1

Synthesis of 3-methyl-1,4-dioxane-2,5-Dione

One mole of chloroacetic acid (94.5 gms.), one mole of D,L-lactic acid (107.0 gms. of 85% water solution), and 8 gms. of Dowex 50W-X ion exchange resin (equivalent to 1 ml. conc. $H_2SO_4$), and 200 ml. benzene were refluxed and the theoretical amount of water collected in a Dean-Stark trap. The solution was allowed to cool to room temperature and the ion exchange resin was filtered off. The benzene was removed on a rotary evaporator with vacuum. The unreacted chloroacetic acid was sublimed out at 0.2 – 0.4 torr. The O-chloroacetyl-D,L-lactic acid was distilled at 108 – 118° C. at 0.2 – 0.3 torr (b.p. ref: U.S. Pat. No. 2,518,456, supra, 113°–118° C. at 0.4 torr,) m.p.: 73°–74° C). After recrystallization from toluene the O-chloroacetyl-D,L-lactic acid has a m.p. of 72°–74° C.

3.34 g. (0.02 mole) O-chloroacetyl-D,L-lactic acid and 2.02 g. (0.02 mole) triethylamine were dissolved in 670 ml. dimethyl formamide. The solution was heated to 100 ± 5° C. for 6 hours and allowed to cool to room temperature. The solvent was distilled off under vacuum yielding a reddish colored semisolid residue. The product was removed by extraction with acetone leaving solid triethylamine hydrochlororide.

The acetone extract was evaporated yielding a reddish colored oil which solidified on standing to a reddish yellow solid. It was recrystallized by dissolving in warm isopropanol and cooling to −25° C. The D,L-3-methyl-1,4-dioxane-2,5-dione had a melting point of 64°–65° C. (0.7 g.). It was further purified by sublimation at 0.01 torr. at 50°–60° C. The yield was 0.3 g., m.p. 63.8°–64.2° C. % Carbon found was 46.57 vs. 46.10 calc'd. % Hydrogen found was 4.73 vs. 4.60 calc'd. The proton nuclear magnetic resonance spectrum of this product in $CDCl_3$ gave the following absorptions where δ (delta) = ppm shift downfield from tetramethyl silane reference absorption; doublet, 3 protons (1.66, 1.72 delta, J = 6 $H_z$); quartet 1 proton ( (4.97), 5.03, 5.10, 5.16 delta, J = 6–7 $H_z$); quartet, 2 protons (4.78, 4.94, 4.96, 5.12 delta, J =16 $H_z$), confirming the structure as 3-methyl-1,4-dioxane-2,5-dione. The product is essentially racemic as would be expected.

NMR Spectrum of 3-methyl-1,4-dioxane-2,5-dione

The proton nuclear mmagnetic resonance spectrum of a chemical compound reveals the number of protons in the molecule that are located in different chemical environments by a series of absorption peaks whose areas are proportional to the number of protons (See, for example, F. A. Bovey, High Resoluton NMR of Macromolecules, Chapter 1, Academic Press, N.Y., 1972). Furthermore, the absorptions are split into multiple peaks by neighboring protons in characteristic ways which further aid in assigning peaks to specific chemical structures (Bovey, pg. 30–32). The spectrum of 3-methyl-1,4-dioxane-2,5-dione:

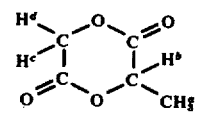

obtained on a 100 megaherz Varian HA-100 spectrometer shows the following absorptions grouped to indicate the splittings of single absorptions into multiplets.

TABLE I

| Position of Line Delta (γ) | Splitting (Herz) | Relative Area | Assignment |
|---|---|---|---|
| 1.66 1.72 | 6 $H_z$ | 3 | 3 $H^a$ protons |
| 5.03 5.10 5.16 | 6 $H_z$ | | $H^b$ protons |
| 4.78 4.94 | 16 $H_z$ | 3 | $H^c$ or $H^d$ |
| 4.96 5.12 | 16 $H_z$ | | $H^c$ or $H^d$ |

A H atom attached to a carbon bearing an oxygen atom, such as $H^a$, is expected to absorb at 1.3-2 delta (Bovey pg. 29). The absorption should be split into two lines separated by 2–13 Herz. (Bovey, pg. 36). The values observed are 1.69 delta (average of doublet) and 6 Herz.

A proton in the environment of $H^b$ should absorb aat higher delta than

because it is influenced by both the $$\begin{array}{c} O \\ \| \\ -C- \end{array} \text{ and } -O-$$

groups, each of which causes a down-field shift from $CH_4$. $H^b$ should be split into 4 lines with a splitting of 6 $H_z$ corresponding to the splitting observed in the $CH_3$ protons. Actually, only 3 lines are observed, but the expected position of the fourth line, (5.03 −06)=4.97 coincides with another strong line of a different origin. Thus, the 3 lines at 5.03, 5.10 and 5.16 delta are assigned to $H^b$.

Protons in the environment of H$^c$ and H$^d$ should absorb at about the same delta as H$^b$ and at first glance H$^c$ and H$^d$ would appear to have identical environments and give a single line. Actually, one must be somewhat nearer than the other to the CH$_3$ group on the opposite side of the ring so the environments differ. The spectrum shows a quartet of lines due to this pair as is expected for two different interacting protons. The splitting of 16 H$_z$ between the first and second lines and between the third and fourth lines is consistent with splittings observed between protons on the same atom. (Bovey, pg. 35). Quartets of this type are not observed in the spectrum of either glycolide or lactide which are tabulated below for comparison.

TABLE II

| Compound | Peak Positions | | |
|---|---|---|---|
| 3-methyl-1,4-dioxane-2,5-dione | 1.66 | 5.03 | 4.73 |
| | 1.72 | 5.10 | 4.94 |
| | | 5.16 | 4.95 |
| | | | 5.12 |
| lactide | 1.66 | 4.94 | |
| | 1.72 | 5.01 | |
| | | 5.07 | |
| | | 5.14 | |
| glycolide | | 4.94 | |

Thus, the NMR spectrum of 3-methyl-1,4-dioxane-2,5-dione is consistent with the assigned structure and inconsistent with any mixture of glycolide and lactide.

EXAMPLE 2

Homopolymerization of 3-methyl-1,4-dioxane-2,5-dione, at 125° C.

In a glass tube was charged 1.0 g. of 3-methyl-1,4-dioxane-2,5-dione prepared as in Example 1 and 0.80 ml. of an ether solution containing 0.1 mg. of SnCl$_2$·2H$_2$O per ml. The ether was vaporized off, and the tube sealed under vacuum. The tube was then placed in a 125° C. oil bath for 80 hours. The tube was cooled, broken open and the contents dissolved in 10 ml. of hexafluoracetone sesquihydrate (HFAS). This solution was added dropwise to 100 ml. of methanol and the resulting precipitated polymer was dried in vacuo for 2 days at room temperature. The resulting polymer weighed 0.6 g. (67% conversion) and had a melting point by differential thermal analysis of 100° C. and an inherent viscosity in HFAS of 0.38 dl/g (0.5 g./100 ml.) at 30° C. The proton NMR spectrum measured in hexafluoracetone sesquideuterate gave the following absorptions where ($\delta$)delta=ppm shift downfield from tetramethylsilane reference absorption: 5.402, 5,332, 4.904, 1,676, 1.605 delta.

Inherent viscosity as used herein is $\eta$ inh=($\ln \eta$ rel/c) where $\eta$ rel is the ratio of the viscosity of a 0.5% (W/V) solution of the polymer in hexafluoracetone sesquihydrate to the viscosity of that solvent alone, and c = 0.5 grams per 100 ml.

NMR Spectrum of Poly(3-Methyl-1,4-Dioxane-2,5-Dione)

The proton nuclear magnetic resonance spectrum of polymers containing glycolic acid units

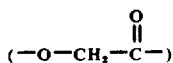

and lactic acid units

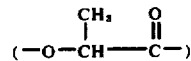

reveals the number of protons which exist in each of the different chemical environments in the polymer chain. For poly(D,L-lactic acid) the methine ( ≡ CH) proton appears as a quartet the center of which is located at 5.286 delta (where delta is the parts per million chemical shift to lower magnetic field from the absorption of the methyl groups in the tetramethyl silane reference standard.) The area of the quartet absorption is one third the area of the methyl absorption as expected. The quartet structure arises due to spin-spin coupling with the protons of the adjoining —CH$_3$ group and further substantiates the assignment.

In a copolymer of D,L-lactide and glycolide containing 52 lactic acid units for each 48 glycolic acid units, two overlapping quartets are seen in the ≡ CH region with centers located as shown in Table III. The quartet centered at 5.276 falls close to that in poly(lactic acid) (5.286) and can be assigned to the methine proton in the center lactic acid unit of the -L-L-L- sequence:

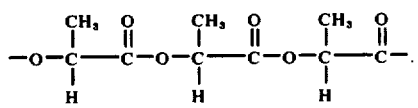

The second quartet in the copolymer is centered at 5,310, very close to the center of the only quartet seen in a 8/92 lactic acid unit/glycolic acid unit copolymer where isolated pairs of lactic acid units should predominate. The 5.310 quartet can thus be assigned to the center methine proton of either a -GLL- or -LLG- sequence:

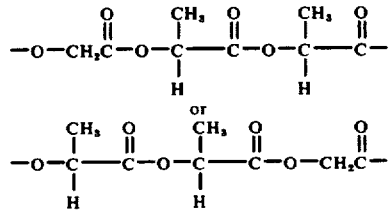

The spectrum of poly(3-methyl-1,4-dioxane-2,5-dione) prepared as in Example 2 shows a quartet absorption centered at 5.367, significantly shifted from absorptions assigned to the -LLL-, -GLL- or -LLG- sequences. The 5.367 absorption can logically be assigned to the center methine proton of the GLG sequence, which is the only other possible sequence of three residues. This is the sequence expected to predominate if polymerization of this monomer occurs by successive attack of the active end group on the least hindered carbonyl group of 3-methyl-1,4-dioxane-2,5-dione to yield -G-L-G-L-G-L- chains. The presence of minor amounts of -GLL- and -LLG- sequences is not ruled out by the NMR spectra as minor absorption at 5.307–5.310 could be masked by the principal methine absorption.

Thus, the position of the lactic acid unit methine absorption reflects the chemical nature of two neighboring units. As the neighbors change from two lactic acid units to one lactic acid unit and then no lactic acid unit, there is a progressive downfield (higher delta) shift of the methine absorption.

become much stronger, showing a tensile strength at break of 17,000 to 21,000 psi. (1,200–1,470 Kg/cm$^2$).

TABLE III

| Polymer | CHEMICAL SHIFT (DELTA) FOR CENTER OF MULTIPLET | | |
|---|---|---|---|
| | ≡CH(quartet) | —CH$_2$ (singlet) | —CH$_3$(doublet) |
| Poly(lactic acid) | 5.286 | — | 1.633 |
| 52/48 mole % copolymer of lactide and glycolide | 5.310 | 5.276 | 4.908 | 1.641 |
| 8/92 mole % copolymer of lactide and glycolide | 5.307 | 4.920 | 1.639 |
| Poly(3,-Methyl-1,4-dioxane 2,5-dione) | 5.367 | 4.907 | 1.643 |
| Sequence assignment | —GLG— | —GLL— and —LLG— | —LLL— |

EXAMPLE 3

Polymerization of D,L-3-methyl-1,4-dioxane-2,5-dione at 220° C.

To a glass tube was charged 0.5 g. of 3-methyl-1,4-dioxane-2,5-dione and 0.1 ml. of an ether solution containing 0.1 mg. of SnCl$_2$·2H$_2$O per ml., and 0.06 ml. of an ether solution containing 20 mg. of lauryl alcohol per ml. The ether was vaporized off and the tube sealed under vacuum. The tube was placed in an oil bath at 220° C. for 2 hours. The tube was cooled, broken open, and the contents dissolved in 5 ml. HFAS. This solution was added dropwise to 50 ml. of methanol and the resulting precipitated polymer was dried in vacuo for two days at 50° C. The resulting poly(D,L-3-methyl-1,4-dioxane-2,5-dione) weighed 0.14 g. and had an inherent viscosity in HFAS of 0.65 dl./g. (0.5 g./100 ml.) at 30° C.

EXAMPLE 4

Polymerization of D,L-3-methyl-1,4-dioxane-2,5-dione at 180° C.

To a glass tube was added 2.0 g. D,L-3-methyl-1,4-dioxane-2,5-dione and 0.4 ml. of an ether solution containing 0.1 mg. of SnCl$_2$·2H$_2$O per ml. The ether was vaporized and removed and the tube sealed under vaccum. The tube was placed in an oil bath at 180°±5° C. and heated for 24 hours. The tube is cooled, broken open and the contents dissolved in 40 ml. of hexafluoroisopropanol (HIPA). This solution was added dropwise to 400 ml. of methanol and the resulting precipitated poly(D,L-3-methyl-1,4-dioxane-2,5-dione) was dried in vacuo for 16 hours at 50° C. The resulting polymer weighed 1.65 g. and had an inherent viscosity in HFAS of 0.83 dl/g (0.5 g./100 ml.) at 30° C.

EXAMPLE 5

Extrusion of Poly(D,L-3-methyl-1,4-dioxane-2,5-dione) as Monofilaments

A 0.5 g. sample of the polymer of Example 4 was placed in the barrel (1 cm i.d.) of a melt-index apparatus (Custom Scientific) fitted with a bottom plug 1 cm. in height and having a 0.5 mm. vertical central hole. A close-fitting weighted piston (4700 g) was placed in the barrel which had been preheated to 160° C. The monofilament which extruded from the hole had a diameter in the range of 0.002 to 0.006 inches (0.05 to 0.15 mm.) and was rather weak. The filaments were drawn by hand to four times their original length on a hot plate having a surface temperature of 50°-60° C. They

EXAMPLE 6

Polymerization of D,L-3-methyl-1,4-dioxane-2,5-dione at 180° C.

To a glass tube was added 6.0 g. of D,L-3-methyl-1,4-dioxane-2,5-dione and 1.2 ml. of an ether solution containing 0.1 mg. of SnCl$_2$·2H$_2$O per ml. The ether was vaporized and removed, and the tube sealed. The sealed tube was placed in an oil bath at 180° ±2° C. for 4 hours, cooled and broken. The cooled tube contents were dissolved in 120 ml. of boiling acetone and the solution added dropwise to 1200 ml. of methanol. The resulting precipitated poly(D,L-3-methyl-1,4-dioxane-2,5-dione) was dried in vacuo for 2 days at 25° C. The resulting polymer weighed 1.4 g. (23% conversion) and had an inherent viscosity in HFAS of 1.19 dl/g(0.5g/100ml) at 30° C.

EXAMPLES 7, 8, and 9

Copolymerization of D,L-3-methyl-1,4-dioxane-2,5-dione with Glycolide

The amounts of D,L-3-methyl-1,4-dioxane-2,5-dione and glycolide indicated in Table IV were combined in glass tubes with 0.80 ml. of an ether solution containing 0.1 mg. of SnCl$_2$·2H$_2$O per ml. and 0.5 ml. of an ether solution containing 20 mg. lauryl alcohol per ml. The ether was vaporized and removed and the tubes sealed under vacuum. The tubes were placed in an oil bath at 220° C. for 2 hours. The contents of each cooled and broken tube were dissolved in HFAS and precipitated in methanol. The precipitated polymer was dried 2 days in vacuo at 50° C.

TABLE IV

| | Example 7 | Example 8 | Example 9 |
|---|---|---|---|
| Mole % D,L-3-methyl-1,4-dioxane-2,5-dione | 10 | 25 | 50 |
| Weight of glycolide used (g) | 3.58 | 2.96 | 1.86 |
| Weight of D,L-3-methyl-1,4-dioxane 2,5-dione used (g) | 0.44 | 1.10 | 2.08 |
| % Conversion to Polymer | 80 | 79 | 25 |
| Melting Point, (Fisher-Johns Apparatus) | 212° C | 188° C | 132° C |
| Inherent Viscosity in HFAS(0.5 mg./ml.) 30° C | 0.45 | 0.32 | 0.18 |
| Mole % D,L-3-methyl-1,4-dioxane 2,5-dione in Polymer (by NMR) | 4.8 | 16.2 | 31.7 |

EXAMPLES 10 and 11

Implantation of Glycolide/D,L-3-Methyl-1,4-Dioxane-2,5-Dione Copolymer in Rabbits The copolymers of Examples 7 and 8 (and polyglycolic acid (PGA), 0.89 inherent viscosity) were formed into strips at room temperature by distributing 0.4 g. of powdered polymer in a die ¾inches deep by ½ inches wide by 3 inches long (1.9 ×1.27 ×7.62 cm) and exerting a hydraulic pressure of 16,000 pounds (7,260kg) on the matched plunger for 30 seconds by means of a Carver hydraulic press. This large pressed piece was cut into 4 strips, each approximately 1.5 inch long, ¼ inch wide (3.8 ×0.63 cm.) and weighing approximately 0.1 g. Each strip was placed in a plastic envelope, vacuum dried, heat sealed, sterilized with ethylene oxide overnight and the residual ethylene oxide was pumped off. Individual strips were then implanted subcutaneously in rabbits. At intervals the rabbits were sacrificed and observed for tissue reaction at the implantation site. The extent of absorption was estimated visually. Tissue reaction was unremarkable in each case. The estimated extent of absorption is shown in Table V.

TABLE V

|  | PGA Control | Example 7 | Example 8 |
|---|---|---|---|
| Mole Ratio of Polymer of D,L-3-methyl-1,4-dioxane-2,5-dione/glycolide | 0/100 | 4.8/95.2 | 16.2/83.8 |
| Absorption at 15 days | 50% | 40–50% | <25% |
| Absorption at 30 days | 90–100% | 100% | 90–100% |
| Absorption at 45 days | 100% | 100% | 100% |

EXAMPLE 12

Implantation of Poly(D,L-3-methyl-1,4-Dioxane-2,5-Dione

Following the procedure of Examples 10 and 11, strips of the poly(D,L-3-methyl-1,4-dioxane-2,5-dione) of Example 6 were prepared and implanted in rabbits. Tissue reaction was unremarkable in each case. The estimated extent of absorption of duplicate samples of these strips and of polyglycolic acid (PGA) control strips is shown in Table VI.

TABLE VI

|  | PGA | Poly(D,L-3-Methyl-1,4-Dioxane-2,5-Dione |
|---|---|---|
| Absorption at 15 days | 50,50% | 0,0% |
| Absorption at 30 days | 85,85% | 50,50% |
| Absorption at 45 days | 100,100% | 85,100% |

EXAMPLE 13

Preparation of O-Chloracetyl-L-Lactic Acid

Into a 2-liter, 2-necked round bottom flask equipped with a magnetic stirrer and a Dean-Stark trap was placed 750 ml. of benzene and 8.0 g. Dowex 50W-X resin. To this suspension 262.2 g. (2.78 mole) of monochloroacetic acid was added. The mixture was refluxed until no further water was collected.

To this was then added 100 g. (1.11 mole) of crystalline L-lactic acid in ten equal portions at a rate such that a subsequent portion was not added until the theoretical amount of water was collected from the preceding portion.

When all water had been collected, heating was discontinued and the resin removed by filtration from the hot solution. The resin was then washed with two 50 ml. portions of hot benzene. The washings were added to the reaction mixture, and the solvent removed in vacuo.

The crude oil which remained was then carefully distilled to remove excess monochloroacetic acid. The remaining oil was then distilled at 95° –105° C./0.05 torr. to give 143.3 g. (77.3%) of O-chloroacetyl-L-lactic acid. This was then redistilled, to give 130 grams (70.3%) of product, b.p. 94° –100° C./0.05 torr.

| Calculated for $ClCH_2-\underset{\underset{O}{\|\|}}{C}-O-\underset{\underset{CH_3}{\|}}{CH}-\underset{\underset{O}{\|\|}}{C}-OH$ | | Found |
|---|---|---|
| C | 36.05 | 35.86 |
| H | 4.24 | 4.41 |
| Cl | 21.29 | 20.74 |
| MW | 166.56 | 173 |

$[\alpha]_D^{25} = -60° \pm 0.7$ (C = 1.34, CHCl$_3$) IR Peaks 3050 cm$^{-1}$, 2975 cm$^{-1}$, 1750 cm$^{-1}$, 1460 cm$^{-1}$, 1412 cm$^{-1}$, 1378 cm$^{-1}$, 1345 cm$^{-1}$, 1315 cm$^{-1}$, 1183 cm$^{-1}$, 1135 cm$^{-1}$, 1095 cm$^{-1}$, 1043 cm$^{-1}$, 957 cm$^{-1}$, 930 cm$^1$, 833 cm$^{-1}$, 788 cm$^{-1}$.

NMR (CDCl$_3$, TMS) singlet 9.53 δ, quartet 5.33, 5.26, 5.19, 5.12 δ, singlet 4.16 δ, doublet 1.64, 1.56 δ.

EXAMPLE 14

Preparation of L-3-methyl-1,4-dioxane-2,5-dione

Forty-five grams (0.270 mole) of O-chloroacetyl-L-lactic acid was dissolved in 4500 ml. of amine-free, dry dimethylformamide. To this solution was added 35.83 ml. (26.0 grams, 0.256 mole) of dry triethylamine. The solution was then heated to 100° C. and kept at this temperature for four hours. At the end of this time, the heating was discontinued and the solvent removed in vacuo to give an oily-semi-solid residue.

The residue was treated with one liter of dry diethyl ether and the insoluble triethylamine hydrochloride filtered off. The ether was then removed in vacuo and the oil taken up in 100 ml. of benzene. The benzene was then extracted with 50 ml. of cold distilled water whose pH was adjusted to 2.5 with HCl. The benzene solution was then quickly dried over anhydrous sodium sulfate and then dried for one hour over molecular sieves. The sieves were filtered off, washed well with 50 ml. of dry benzene, the combined solvent and washings were then removed in vacuo to give 16.9 grams (51%) of an oil which was crystallized from isopropanol at −20° C. The semi-solid was filtered cold and quickly recrystallized from a minimum volume of boiling isopropanol. Two additional recrystallizations from isopropanol gave a white solid, L-3-methyl-1,4-dioxane-2,5-dione, m.p. 38° –39° C., 8.0 grams (24%).

IR Peaks 3450 cm$^{-1}$, 1775 cm$^{-1}$, 1448 cm$^{-1}$, 1378 cm$^{-1}$, 1345 cm$^{-1}$, 1296 cm$^{-1}$, 1225 cm$^{-1}$, 1195 cm$^{-1}$, 1130 cm$^{-1}$, 1099 cm$^{-1}$, 1053 cm$^{-1}$, 1036 cm$^{-1}$, 958 cm$^{-1}$, 849 cm$^{-1}$, $[\alpha]_D^{25} = -245°$ ($\pm 1.0°$) (C=0.988, benzene)

NMR (CDCl$_3$, TMS) Quartet (5.00, 5.06, 5.14, 5.20 δ), doublet (4.98, 4.94 δ), doublet (1.70, 1.64 δ)

EXAMPLE 15

Preparation of Poly-L-3-methyl-1,4-dioxane-2,5-dione

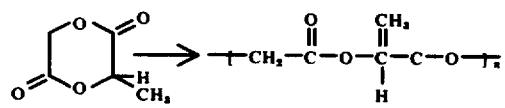

0.5 grams of L-3-methyl-1,4-dioxane-2,5-dione from Example 14 was polymerized in the presence of 0.002 weight percent of stannous chloride dihydrate over a twenty-four hour period at 180° C. to give 0.5 grams of polymer, IV=0.33, and softening point 56°–60° C.

EXAMPLES 16 and 17

Copolymerization of L-3-methyl-1,4-dioxane-2,5-dione with Glycolide

Polymerization tubes were charged with the quantities of monomers indicated in Table VII and 0.002% SnCl$_2$·2H$_2$O by weight based on total monomers was added in an ethereal solution. The ether was evaporated and the tube sealed under vacuum. The tubes were heated in an oil bath for 24 hours at 190° C.

The tubes were removed, chilled in dry ice-acetone, cracked open and dissolved in HFAS. The polymer was then precipitated from solution with methanol, filtered and dried overnight in a vacuum oven.

TABLE VII

|  | Example 16 | Example 17 |
|---|---|---|
| Mole % of L-3-methyl-1,4--dioxane-1,5-dione | 15 | 25 |
| Mole % Glycolide | 85 | 75 |
| Gms. L-3-methyl-1,4--dioxane-1,5-dione | 0.5 | 0.5 |
| Gms. glycolide | 2.53 | 1.34 |
| Melting Point (Differential Thermal Analysis at 10° C./min.) | 196° C. | 175° C. |
| Inherent Viscosity in HFAS (0.5 mg./ml.) 30° C. | 0.53 | 0.60 |
| Mole % L-3-methyl-1,4--dioxane-2,5-dione in Copolymer | 7.2 | 12.4 |
| Yield % | 78 | 83 |

EXAMPLE 18

Preparation of 3,3-dimethyl-1,4-dioxane-2,5-dione

To a flask containing two liters of chloroform, 1 mole of 2-hydroxy-isobutyric acid (104.1 gms.) and 2.2 moles of triethylamine (224 gms.), cooled in an ice bath, was slowly added 1 mole of chloroacetyl chloride (127 gms.) Addition took one hour. The chloroform was evaporated to yield a reddish semi-solid which was triturated several times with acetone followed by decantation of the reddish acetone extract. The white solid residue was triethylamine hydrochloride. The acetone extracts were combined and concentrated under vacuum to a red oil which was distilled under vacuum. The fraction distilling at 103°–110° C./0.7–0.9 torr. was collected. This fraction solidified to a green semi-solid which was recrystallized from isopropyl alcohol and then sublimed at 75° C./0.1 torr. to yield 15 grams of white solid, m.p. 82°–83° C. This was dissolved in 3000 ml. of benzene at 10° C. and extracted successively with three 300 ml. portions of 0.01 N HCl solution saturated with sodium chloride in a separatory funnel, and the benzene layer quickly dried by filtration through a bed of anhydrous sodium sulfate into a flask containing anhydrous magnesium sulfate. After the removal of the magnesium sulfate by filtration and the benzene under vacuum, the solid 3,3-dimethyl-1,4-dioxane-2,5-dione was recrystallized from isopropyl alcohol and sublimed at 75° C/0.1 torr. to yield 13 grams of solid, m.p. 85°–86° C., % C found = 50.00 vs. 50.00 calculated, % H found = 5.52 vs. 5.60 calculated.

The proton NMR spectrum of this example in CDCl$_3$ gave the following absorptions where δ = ppm shift downfield from the tetramethylsilane reference absorption: singlet, 6 protons at 1.72 δ and singlet, 2 protons at 5.02 δ.

EXAMPLES 19, 20 AND 21

Copolymerization of Glycolide and 3,3-Dimethyl-1,4-dioxane-2,5-dione

To 3 glass tubes were added the amounts of glycolide and 3,3-dimethyl-1,4-dioxane-2,5-dione indicated in Table VIII. To each tube was added 1.2 ml. of an ether solution of SnCl$_2$·2H$_2$O (0.1 mg./ml.) and 0.75 ml. of an ether solution of lauryl alcohol (10 mg./ml.). The ether was evaporated off, and tubes were evacuated and sealed, then heated for 2 hours at 220° C in an oil bath. After cooling and breaking, the tube contents were dissolved in 20 ml. of hexafluoroacetone sesquihydrate per gram of recovered solid. The polymer solution was added to 10 times its volume of methanol. The precipitated polymer was then extracted for two days in a Sohxlet extracter with acetone. The undissolved polymer was vacuum-dried at 50° C. for 24 hours.

TABLE VIII

|  | Ex. 19 | Ex. 20 | Ex. 21 |
|---|---|---|---|
| (A) Glycolide, gms. | 5.27 | 4.60 | 3.95 |
| (B) 3,3-Dimethyl-1,4--dioxane-2,5-dione | 0.74 | 1.45 | 2.05 |
| Mole ratio (A)/(B) in feed | 90/10 | 80/20 | 70/30 |
| % Conversion | 82 | 76 | 64 |
| Inherent Viscosity (I.V.) | 0.54 | 0.45 | 0.44 |
| Mole % B in polymer | 2.1 | 4.5 | 6.0 |

EXAMPLE 22

Copolymerization of D,L-Lactide with D,L-3-Methyl-1,4-Dioxane-2,5-Dione in 90/10 Mole Ratio To a polymerization tube was added 0.54 grams of D,L-3-methyl-1,4-dioxane-2,5-dione (0.00415 mole) and 5.41 g. of D,L-lactide (0.0376 mole), 1.20 ml. of an ether solution of SnCl$_2$·2H$_2$O (0.1 mg./ml.) and 0.75 ml. of an ether solution of lauryl alcohol (10 mg./ml.). The ether was vaporized and removed. The tube was evacuated, sealed and heated for 24 hours at 180° C. The cooled tube contents were dissolved in boiling acetone and the resulting solution was added to methanol. The resulting solid was collected and vacuum dried at 50° C. for 24 hours. The conversion of monomers to polymer was 79% by weight and the polymer inherent viscosity was 1.36. The mole % of D,L-3-methyl-1,4-dioxane-2,5-dione units in the polymer was 7.9 by NMR.

EXAMPLE 23

Copolymerization of D,L-Lactide with D,L-3-Methyl-1,4-Dioxane-2,5-Dione in 80/20 Mole Ratio To a polymerization tube was added 1.21 g. of D,L-3-methyl-1,4-dioxane-2,5-dione (0.00931 mole) and 4.86 g. of D,L-lactide (0.0338 mole). The procedure was then identical to Example 22. The conversion of monomers to polymer was 74% by weight, and the polymer inherent viscosity was 1.24. The polymer contained 14.7 mole percent of units derived from D,L-3-methyl-1,4-dioxane-2,5-dione by NMR.

EXAMPLE 24

Copolymerization of L-Lactide with D,L-3-Methyl-1,4-Dioxane-2,5-Dione in 90/10 Mole Ratio Example 22 was repeated substituting L(-) lactide for D,L-lactide. Conversion was 78%, inherent viscosity 0.73 and the polymer contained 7.6 mole % of units derived from D,L-3-methyl-1,4-dioxane-2,5-dione by NMR.

EXAMPLE 25

Copolymerization of L-Lactide with D,L-3-Methyl-1,4-Dioxane-2,5-dione in 80/20 Mole Ratio Example 23 was repeated substituting L(-)-lactide for D,L-lactide. Conversion was 75%, inherent viscosity 0.61 and the polymer contained 10.2 mole % of units derived from D,L-3-methyl-1,4-dioxane-2,5-dione by NMR.

EXAMPLE 26

Preparation of O-Chloroacetyl-L-Lactic Acid

A mixture of 57.6 grams (0.4 mole) of sublimed L-lactide, 378.0 grams (4.0 mole) of monochloroacetic acid and 2.8 grams of antimony trioxide was heated in an oil bath for 8 hours at 180° C., then for 24 hours at 130° C., and finally for 5 hours at 185° C. The excess monochloroacetic acid was then distilled off in vacuo and the O-chloroacetyl-L-lactic acid produced distilled at 90°-110° C./0.05 torr. to give 109.3 grams (82%) of product. The product was then slowly redistilled at 94°-100° C./0.05 torr. to give 100.5 grams (75.4%) of O-chloroacetyl-L-lactic acid, identical to that prepared from L-lactic acid and monochloroacetic acid.

If 3.1 grams of titanium dioxide is used in place of antimony trioxide, the yield is 69.2 grams of product (51.9%). Tetraisopropyl titanate may also be used as a catalyst.

EXAMPLE 27

Preparation of O-Chloroacetyl-D,L-lactic acid from Poly-D,L-Lactic Acid 530.1 gms. (5.55 mole) of monochloroacetic acid, 100 gms. (1.39 equiv.) of poly-D,L-lactic acid and 1.5 gms. of antimony trioxide was heated with stirring at 160° C. for twenty-four hours. The excess monochloroacetic acid was then distilled off in vacuo and the product distilled at 85°-100° C/0.075 torr. to give 122.5 gms. (53%) of O-chloroacetyl-D,L-lactic acid. The material so recovered was identical to that prepared from D,L-lactic acid and monochloroacetic acid.

EXAMPLE 28

Preparation of D,L-3-Methyl-1,4-Dioxane-2,5-Dione from Glycolic Acid and D,L-Lactic acid To 543 g. of 70% aqueous solution of glycolic acid was added 276 g. of an 85% aqueous solution of D,L-lactic acid. This mixture was heated in a distillation apparatus at atmospheric pressure until water had ceased to distill. Then, 6 g. of antimony trioxide was added and heating was continued at 10 torr. until 350 g. of distillate was obtained (head temperature range 120°-180° C.). This distillate was refractionated using a Vigreaux column at 10 torr. to give 40 g. of fraction A (b.p. 114°-140° C.) and 160 g. of fraction B (b.p. 142°-153° C.). Fraction B partially solidified at 5° C. and was recrystallized from 320 ml. of isopropyl alcohol.

The recrystallized material was further fractionated using a Vigreaux column to yield the fractions shown in Table IX. The fractions were analyzed by a gas chromatographic method.

TABLE IX

| Fraction Number | Weight grams | B.P. (10 Torr.) | Product Composition Glycolide | Lactide | (Weight Percent) D,L. M.D.D. |
|---|---|---|---|---|---|
| 1 | 20 | 142–144° C. | 8 | 22 | 70 |
| 2 | 54 | 144–146 | 10 | 13 | 77 |
| 3 | 10 | 146–148 | 17 | 7 | 76 |

EXAMPLE 29

Preparation of D,L-3-Methyl-1,4-Dioxane-2,5-Dione from Glycocolic Acid and D,L-Lactic Acid Example 28 is repeated until Fraction B is obtained by distillation. This fraction is then fractionated in a high-efficiency distillation apparatus to obtain D,L-3-methyl-1,4-dioxane-2,5-dione with a purity greater than 99 percent as measured by gas chromatography.

The choice of L-, D-, or D, L- components in the feed to the polymerization determines the optical activity of the units in the polymer. The properties tend toward those resulting from greater crystallinity if a single optical isomer is used in the polymer.

The rate of tissue absorption in living mammals is affected by the hydrolytic history of the polymers before implantation, the molecular weight, and the size and shape of the implanted polymer, as well as the chemical composition of the polymer. In general, subject to the effect of these other variables, the higher proportion of glycolic acid units, the more rapid the absorption. The drier the polymer is kept, the slower the absorption, and the higher the molecular weight, the stronger the polymer.

The use of the present homopolymers and co-polymers permits an increase in the range of absorption characteristics available for surgical devices.

We claim:

1. A method of forming a polymer containing more than 2% by weight of recurring units of the formula:

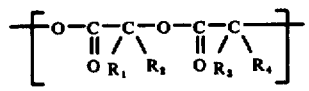

and the remaining units are

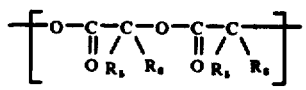

where $R_1$ and $R_2$ are not the same as $R_3$ and $R_4$, $R_1$ has at least one carbon atom, and $R_1$, $R_2$, $R_3$, $R_4$, $R_5$, and $R_6$, are separately selected from the group consisting of hydrogen and the radicals methyl, ethyl, propyl, isopropyl, butyl, isobutyl, cyclohexyl, and phenyl which comprises heating, in the presence of a catalyst, at least 2% by weight of an unsymmetrically substituted 1,4-dioxane-2,5-dione of the formula:

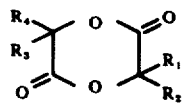

where $R_1$, $R_2$, $R_3$ and $R_4$ are defined as above and at least one compound of the formula:

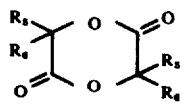

where $R_5$ and $R_6$ are defined as above.

2. The method of claim 1 which comprises treating 3-methyl-1,4-dioxane-2,5-dione and glycolide with a tin chloride dihydrate catalyst until polymerized.

3. A polymer containing more than 2% by weight of recurring units of the formula:

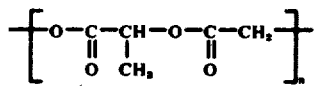

and the remaining units are

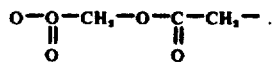

where $R_1$ is $CH_3$- or H-.

4. The polymer of claim 3 which has the formula:

$$\left[\text{O}-\underset{\underset{\text{O}}{\|}}{\text{C}}-\underset{\underset{\text{CH}_3}{|}}{\text{CH}}-\text{O}-\underset{\underset{\text{O}}{\|}}{\text{C}}-\text{CH}_2\right]_n$$

and $n$ is such that the weight average molecular weight is at least about 5,000.

5. The polymer of claim 3 containing 50 or more % by weight of recurring units of the formula:

$$\text{O}-\underset{\underset{\text{O}}{\|}}{\text{C}}-\text{CH}_2-\text{O}-\underset{\underset{\text{O}}{\|}}{\text{C}}-\text{CH}_2-.$$

* * * * *